US012661359B2

(12) United States Patent
Taub

(10) Patent No.: US 12,661,359 B2
(45) Date of Patent: Jun. 23, 2026

(54) THERAPEUTIC COMBINATIONS OF ROSUVASTATIN AND RESMETIROM FOR THE TREATMENT OF LIVER DISORDERS OR LIPID DISORDERS

(71) Applicant: Madrigal Pharmaceuticals, Inc., West Conshohocken, PA (US)

(72) Inventor: Rebecca Taub, Villanova, PA (US)

(73) Assignee: Madrigal Pharmaceuticals, Inc., West Conshohocken, PA (US)

( * ) Notice: Subject to any disclaimer, the term of this patent is extended or adjusted under 35 U.S.C. 154(b) by 380 days.

(21) Appl. No.: 18/263,546

(22) PCT Filed: Jan. 28, 2022

(86) PCT No.: PCT/US2022/014384

§ 371 (c)(1),
(2) Date: Jul. 31, 2023

(87) PCT Pub. No.: WO2022/165227

PCT Pub. Date: Aug. 4, 2022

(65) Prior Publication Data

US 2024/0307405 A1 Sep. 19, 2024

Related U.S. Application Data

(60) Provisional application No. 63/143,977, filed on Feb. 1, 2021.

(51) Int. Cl.

| | |
|---|---|
| ***A61K 31/53*** | (2006.01) |
| ***A61K 31/505*** | (2006.01) |
| ***A61P 3/06*** | (2006.01) |

(52) U.S. Cl.

CPC ............ *A61K 31/53* (2013.01); *A61K 31/505* (2013.01); *A61P 3/06* (2018.01)

(58) Field of Classification Search

CPC .......... A61K 31/53; A61K 31/505; A61P 3/06
See application file for complete search history.

(56) References Cited

U.S. PATENT DOCUMENTS

| | | | |
|---|---|---|---|
| 6,858,618 B2 | 2/2005 | Raza et al. |
| 7,452,882 B2 | 11/2008 | Haynes et al. |
| 9,266,861 B2 | 2/2016 | Hester et al. |
| 2020/0390858 A1 | 12/2020 | DePaoli et al. |

FOREIGN PATENT DOCUMENTS

| | | |
|---|---|---|
| WO | 2018/075650 A1 | 4/2018 |

OTHER PUBLICATIONS

Feb. 8, 2018, Madrigal Press Release (Year: 2018).*

Anonymous: “Madrigal’s MGL-3196 Achieves Primary Endpoint in Patients With Heterozygous Familial Hypercholesterolemia (HeFH)”, Drug Development & Delivery, Jan. 1, 2018, pp. 1-5.

Antonopoulos et al: “Rosuvastatin as a novel treatment of non-alcoholic fatty liver disease in hyperlipidemic patients”, ATHEROSCLEROSIS, vol. 184, No. 1, Jan. 1, 2006, pp. 233-234.

Harrison et al: “Resmetirom (MGL-3196) for the treatment of non-alcoholic steatohepatitis: a multicentre, randomised, double-blind, placebo-controlled, phase 2 trial”, The Lancet, vol. 394, No. 10213, Nov. 11, 2019, pp. 2012-2024.

Harrison et al: “Resmetirom (MGL-3196) for the treatment of non-alcoholic steatohepatitis: a multicentre, randomised, double-blind, placebo-controlled, phase 2 trial”, The Lancet, vol. 394, No. 10213, Nov. 11, 2019, supplementary appendix, pp. 1-17.

Jakobsson et al,. “Potential Role of Thyroid Receptor B Agonists in the Treatment of Hyperlipidemia”, Drugs,. vol. 77,.Sep. 2, 2017, pp. 1613-1621.

Kastelein et al: “LDL cholesterol, apolipoprotein B, lipoprotein(a), apolipoprotein CIII and triglyceride lowering by MGL-3196, a thyroid hormone beta selective agonist, in a 12 week study in HeFH patients”, European Heart Journal, Aug. 1, 2018, pp. 1105-1106.

International Search Report and Written Opinion for International Application No. PCT/US2022/014384, Apr. 22, 2022 (14 pages).

* cited by examiner

*Primary Examiner* — Timothy R Rozof
(74) *Attorney, Agent, or Firm* — Venable LLP

(57) ABSTRACT

The present disclosure provides a combination therapy for treating a liver disease or disorder and/or a lipid disease or disorder in a subject in need thereof. Specifically, the combination therapy comprises administration of rosuvastatin and resmetirom to a subject in need thereof.

13 Claims, 8 Drawing Sheets

THERAPEUTIC COMBINATIONS OF ROSUVASTATIN AND RESMETIROM FOR THE TREATMENT OF LIVER DISORDERS OR LIPID DISORDERS

CROSS-REFERENCE TO RELATED APPLICATIONS

The present application is a U.S. National Phase application, filed under 35 U.S.C. § 371, of International Application No. PCT/US2022/014384, filed Jan. 28, 2022, which claims benefit of and priority to U.S. Provisional Patent Application No. 63/143,977, filed Feb. 1, 2021, the entire contents of each of which are hereby incorporated by reference in their entirety.

FIELD OF THE DISCLOSURE

The present disclosure relates to therapeutic combinations for treating a liver disease or disorder and/or a lipid disease or disorder in a subject.

BACKGROUND

Non-alcoholic steatohepatitis (NASH) is the most common chronic liver disease in the United States. NASH is a fatty inflammation of the liver and a major cause of cirrhosis, fibrosis and liver failure. The disease is progressive, starting as steatosis or nonalcoholic fatty liver disease (NAFLD), progressing to an inflamed fatty liver (NASH), and eventually leading to cirrhosis and fibrosis. The disease is generally asymptomatic until severe liver impairment occurs.

The prevalence of NAFLD in the U.S. population is about 20-23%, and may be as high as 33%, and the prevalence of NASH in the U.S. population is about 2-3%. Some NASH patients will progress to late stage disease: approximately 15-50% of NASH patients progress to severe fibrosis, and approximately 7-16% progress to cirrhosis. The rate of liver-specific mortality in NASH cirrhotics is approximately 10% per decade.

Currently, no specific therapies for NASH exist.

Despite advances in treatment, approximately 70% of high-risk cardiovascular (CV) patients do not achieve low-density lipoprotein cholesterol (LDL-C) goals, and as many as 10% of hypercholesterolemic patients do not tolerate statins. Elevated LDL-C levels are associated with CV diseases, including myocardial infarctions and strokes, and drugs such as statins that lower LDL-C can also reduce CV morbidity and mortality.

Familial hypercholesterolemia is underdiagnosed and undertreated in the general population. Heterozygous familial hypercholesterolemia (HeFH) and homozygous familial hypercholesterolemia (HoFH) are genetic disorders characterized by severe debilitating dyslipidemia and early onset CV disease. Individuals with HeFH typically have LDL-C levels approximately double that of unaffected siblings. HeFH is most commonly caused by mutations of the low-density lipoprotein receptor (LDLR) gene. If untreated, early onset coronary artery disease will likely develop in HeFH patients. The prevalence of HeFH is estimated to be 1 in 500 and may be as high as 1 in 200. Despite treatment with newer therapies (e.g., proprotein convertase subtilisin/kexin type 9 [PCSK9] inhibitors) and standard care (which includes statins and ezetimibe), some HeFH patients are not achieving their LDL-C goal. A recent retrospective study of HeFH patients followed over two decades revealed that only 18.8% of the patients receiving maximal therapy (i.e., statins with a potency of >45% LDL-C reduction plus at least another lipid-lowering agent) reach target LDL-C levels of <100 mg/dL.

There exists an urgent unmet need to develop new methods of treating liver disorders and lipid disorders.

SUMMARY

In some aspects, the present disclosure pertains, at least in part, to a method for treating a liver disorder or a lipid disorder.

In some aspects, the present disclosure pertains, at least in part, to a method for treating a liver disorder or a lipid disorder by administering to a subject in need thereof a combination therapy comprising rosuvastatin and resmetirom. Rosuvastatin and resmetirom can be administered in the same composition or different compositions. Rosuvastatin and resmetirom can also be administered simultaneously or in temporal proximity.

In some embodiments, rosuvastatin is administered in a range of about 1 mg to 40 mg.

In some embodiments, resmetirom is administered in a range of about 40 to 200 mg.

In some embodiments, the present disclosure provides a method of treating a liver disorder or a lipid disorder in a subject in need thereof, the method comprising administering to the subject rosuvastatin in a range of about 1 mg to 40 mg, and resmetirom in a range of about 40 mg to 200 mg.

In some embodiments, the present disclosure provides a method of treating a liver disorder or a lipid disorder in a subject in need thereof, the method comprising administering to the subject a pharmaceutical composition comprising rosuvastatin in a range of about 1 mg to 40 mg, resmetirom in a range of about 40 mg to 200 mg, and a pharmaceutically acceptable excipient.

In some embodiments, the present disclosure provides the use of rosuvastatin and resmetirom in the manufacture of a medicament for treating a liver disorder or a lipid disorder in a subject in need thereof, wherein the medicament comprises a first medicament and a second medicament that is separated from the first medicament, the first medicament including rosuvastatin in a range of about 1 mg to 40 mg, and the second medicament including resmetirom in a range of about 40 mg to 200 mg.

In some embodiments, rosuvastatin is administered at about 2 mg, about 4 mg, about 6 mg, about 8 mg, about 10 mg, or about 12 mg.

In some embodiments, resmetirom is administered at about 40 mg, about 50 mg, about 60 mg, about 70 mg, about 80 mg, about 90 mg, about 100 mg, or about 110 mg.

In some embodiments, rosuvastatin is formulated in a gel, a tablet, a pill, or a capsule.

In some embodiments, resmetirom is formulated in a gel, a tablet, a pill, or a capsule.

In some embodiments, rosuvastatin and resmetirom are administered orally.

In some embodiments, rosuvastatin and resmetirom are administered once daily. In some embodiments, rosuvastatin and resmetirom are administered twice daily. In some embodiments, rosuvastatin and resmetirom are administered three times daily.

In some embodiments, the liver disorder is nonalcoholic steatohepatitis (NASH) or fatty liver disease.

In some embodiments, the lipid disorder is selected from the group consisting of dyslipidemia, hyperlipidemia, hypertriglyceridemia, hypercholesterolemia, low HDL, and high LDL. In some embodiments, the hypercholesterolemia is heterozygous familial hypercholesterolemia (HeFH) or homozygous familial hypercholesterolemia (HoFH).

In some embodiments, the subject has a cardiovascular risk.

In some embodiments, the subject has a hepatic impairment.

In some embodiments, the subject is a mammal.

In some embodiments, the subject is a human.

In some embodiments, the subject is not currently administered atorvastatin.

In some aspects, the present disclosure provides a pharmaceutical composition comprising rosuvastatin in a range of about 1 mg to 40 mg, resmetirom in a range of about 40 mg to 200 mg, and a pharmaceutically acceptable excipient.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the disclosure will be apparent from the following detailed description and claims.

DETAILED DESCRIPTION

Figure 1:
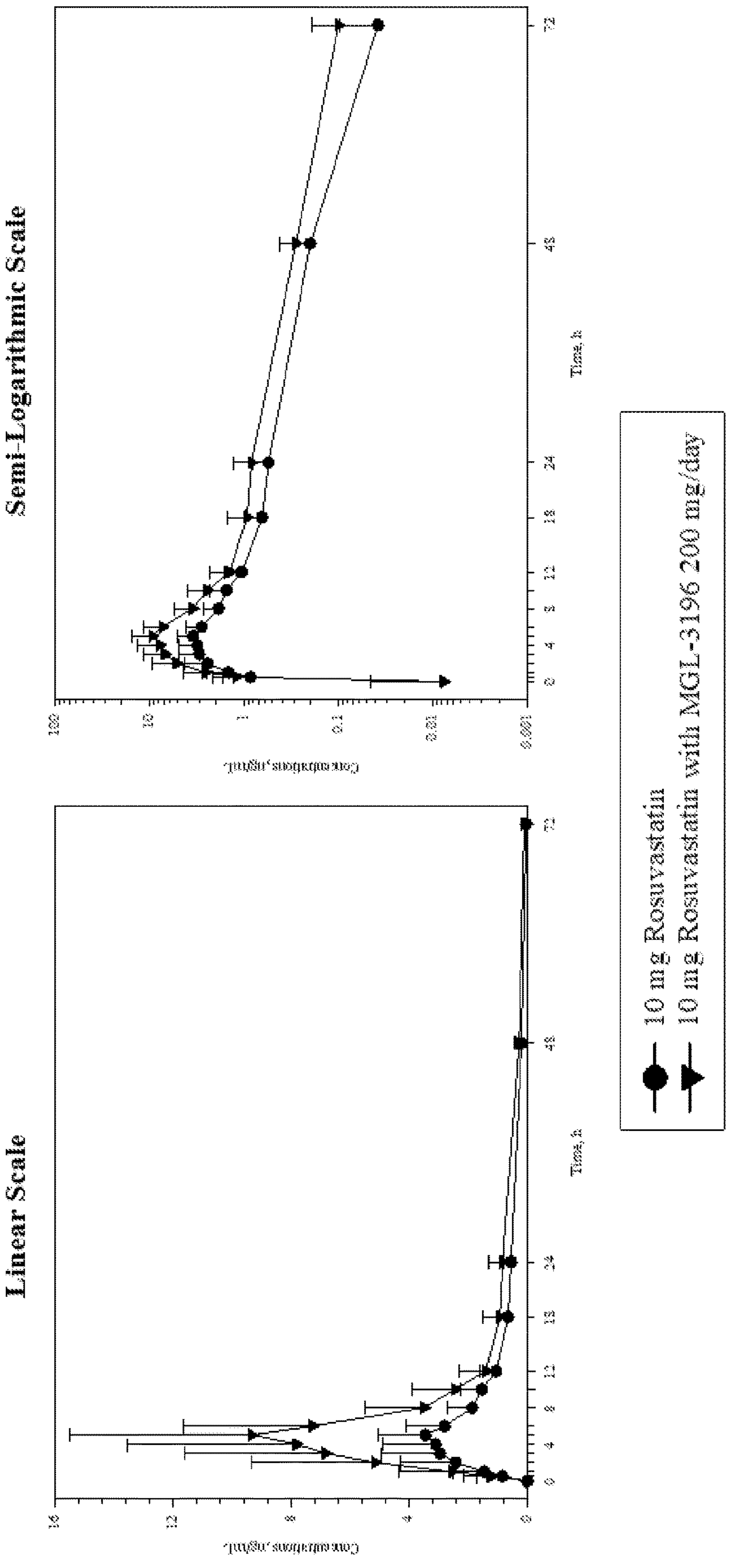
FIG. 1 is a graph showing mean (SD) plasma concentration-time profiles of rosuvastatin in healthy subjects following a 10 mg rosuvastatin dose with or without 200 mg/day MGL-3196.

The present disclosure is related to the use of resmetirom and rosuvastatin to treat a liver disease or disorder and/or a lipid disease or disorder. The present disclosure is related to the use of resmetirom and rosuvastatin to prevent a liver disease or disorder and/or a lipid disease or disorder.

Rosuvastatin or a pharmaceutically acceptable salt thereof is an HMG-COA reductase inhibitor that inhibits the synthesis of cholesterol, which is used to treat dyslipidemia. Crestor® tablets (rosuvastatin calcium salts developed by AstraZeneca), including rosuvastatin as a main ingredient, have been widely used for the treatment of dyslipidemia and dyslipidemia-related disorders. In particular, the success of rosuvastatin in lowering LDL cholesterol levels in blood and increasing beneficial HDL cholesterol levels in vivo has been reported. Atorvastatin (or simvastatin), which is commercially available as a drug having the same mechanism as rosuvastatin, has not achieved similar success.

While statins, such as atorvastatin or rosuvastatin, are effective at lowering LDL-C, in general, they are not effective at lowering triglyceride levels. Some statins can significantly lower triglyceride levels when administered at high doses, e.g., atorvastatin at 80 mg. However, high dose statin therapy can cause muscle pain (myalgia) and is often not well tolerated by patients. In addition, high dose statin therapy carries with it an increased risk for serious muscle toxicity such as rhabdomyolysis.

In 2011, the Food and Drug Administration (FDA) mandated safety-labeling changes limiting the use of high dose (80 mg) simvastatin due to safety concerns of muscle injury or myopathy. Although myopathy events are rare, a more widespread problem is various muscle side effects such as pain and weakness, particularly at high doses, leading to poor tolerability and lack of persistence on statin therapy.

Further, because certain statins are metabolized by cytochrome P450 enzymes which also mediate metabolism of other drugs, the use of higher doses of statins may be contraindicated for use with certain other therapies.

Resmetirom is a thyroid hormone receptor (THR) β-selective agonist. Disclosures related to resmetirom can be found in U.S. Pat. No. 9,266,861, U.S. patent application Ser. No. 16/343,065, and PCT Application Serial No. PCT/US2019/040276, the contents of each of which are incorporated herein by reference in their entireties.

Preclinical, toxicology, phase 1, and phase 2 clinical data suggest resmetirom has a differentiated profile as a potential treatment for non-alcoholic steatohepatitis (NASH), non-alcoholic fatty liver disease (NAFLD), and associated dyslipidemias.

Resmetirom showed a clean safety profile. THR-β selectivity enhances the safety profile of resmetirom, compared to non-selective agents. Resmetirom has shown neither suppression of the central thyroid axis nor THR-α effects on heart rate or bone, and it reduces elevated liver enzymes in NASH patients.

A phase 2 clinical study (NCT02912260) showed that as compared to a placebo, resmetirom is effective in: (a) reducing hepatic fat after 12 weeks and 36 weeks of treatment in patients with NASH; (b) reducing several atherogenic lipids and lipoproteins, notably LDL cholesterol, apolipoprotein B, triglycerides, lipoprotein(a), and apolipoprotein CIII; and (c) improving markers of liver injury and fibrosis. See Harrison et al., *The Lancet* 394.10213 (2019): 2012-2024, the contents of which are incorporated herein by reference in their entireties.

Additionally, a phase 2 clinical study (NCT03038022) carried out on patients with heterozygous familial hypercholesterolemia (HeFH) showed that resmetirom lowers the LDL-C compared to a placebo. LDL-C lowering reached 28.5% compared to placebo in a prespecified group of resmetirom-treated patients intolerant of high intensity statin doses.

Notably, a combination therapy comprising rosuvastatin and resmetirom for treating a liver disorder or a lipid disorder has not been investigated. Without wishing to be bound by theory, resmetirom facilitates the absorption of rosuvastatin in the intestine through the BCRP transporter and potentially reduces the elimination of rosuvastatin from the liver. As such, the combination therapy described herein can allow for lower doses of rosuvastatin than what is currently prescribed, thereby reducing or eliminating the side effects (e.g., myopathy) of high dose rosuvastatin.

To evaluate a compound (e.g., MGL-3196 or rosuvastatin) as a potential substrate for human OSTαβ-mediated transport, cells transfected with OSTαβ can be used in comparison with control cells. Transfected cells and control cells are both exposed to the compound, and the concentration of the compound in the transfected cells and the control cells are then measured. An uptake ratio can then be calculated to quantify the difference of the concentration, indicating whether OSTαβ mediates the transport of the compound.

Methods of Treatment Prevention

In some aspects, the present disclosure pertains, at least in part, to a method for treating a liver disease or disorder or a lipid disease or disorder.

In some aspects, the present disclosure pertains, at least in part, to a method for treating a liver disorder or a lipid disorder by administering to a subject in need thereof a combination therapy comprising rosuvastatin and resmetirom.

In some embodiments, the liver disease or disorder treated by the methods of the present disclosure is fatty liver disease.

In some embodiments, the liver disease or disorder treated by the methods of the present disclosure is NAFLD. Two types of NAFLD are simple fatty liver and NASH. NAFLD refers to a wide spectrum of liver diseases ranging from simple fatty liver (steatosis), to NASH, to cirrhosis. All of the stages of NAFLD have in common the accumulation of fat in the hepatocytes. NASH is a form of NAFLD in which the subject also has hepatitis. More specifically in NASH, the fat accumulation is associated with varying degrees of inflammation (hepatitis) and scarring (fibrosis) of the liver. NAFLD and NASH occur in individuals who do not consume excessive amounts of alcohol. Yet, in many respects, the histological picture of an NAFLD biopsy is similar to what can be seen in liver disease caused by alcohol abuse. NAFLD and NASH are considered the primary fatty liver diseases. The secondary fatty liver diseases include those that occur in other types of liver disease. Thus, alcoholic liver disease (ALD) is the most frequent secondary fatty liver disease. Secondary fatty liver can also occur in chronic viral hepatitis C (HCV), chronic viral hepatitis B (HBV), chronic autoimmune hepatitis (AIH), and Wilson's disease.

The symptoms of NAFLD and NASH are usually not dramatic and tend to be non-specific (e.g., they can also be observed in other diseases). The symptoms are minimal in most patients, who may, however, experience occasional, vague right upper-quadrant abdominal pain. This pain characteristically is dull and aching, without a predictable pattern of occurrence. It is not an intense, sudden, and severe pain, as might occur with, for example, gallstones. The abdominal pain in NAFLD and NASH is thought to be due to the stretching of the liver covering (capsule) when the liver enlarges and/or when there is inflammation in the liver. In contrast to ALD, hepatitis B, or hepatitis C, symptoms of severe, acute liver failure (e.g., jaundice, intense fatigue, loss of appetite, nausea, vomiting, and confusion) are not observed in NAFLD or NASH. Obesity and related conditions (e.g., diabetes, hypertension) are frequently seen among those suffering from NAFLD or NASH, and the classic signs of insulin resistance often dominate the physical exam in NAFLD and NASH. *Acanthosis nigricans*, a dark pigmentation of the skin of the armpits and neck, can be a sign of insulin resistance and is frequently seen in children with NASH. When the liver is palpated, it usually feels normal. However, when very large amounts of fat accumulate in the liver, it can become quite large with a soft, rounded edge that can be easily felt by the doctor.

In addition to the symptoms described above, a diagnosis of NAFLD or NASH can be made based on the following criteria: clinical and/or biochemical signs of insulin resistance; chronically elevated alanine aminotransferase (ALT); signs of fatty liver on ultrasound; exclusion of other causes of elevated ALT and fatty liver. Only a liver biopsy, however, can establish a definite diagnosis and determine the severity of NAFLD or NASH.

In some embodiments, the liver disease or disorder treated by the methods of the present disclosure is NASH.

In some embodiments, the lipid disease or disorder treated by the methods of the present disclosure is selected from the group consisting of dyslipidemia, hyperlipidemia, hypertriglyceridemia, hypercholesterolemia, low HDL, and high LDL. In some embodiments, the hypercholesterolemia is heterozygous familial hypercholesterolemia (HeFH) or homozygous familial hypercholesterolemia (HoFH).

In some embodiments, the subject has a cardiovascular risk. In some embodiments, the subject has a risk for developing the liver disease or disorder described herein. In some embodiments, the subject has a risk for developing the lipid disease or disorder described herein.

In some embodiments, the subject has a THRβ mutation selected from the group consisting of a substitution of threonine (T) for the wild type residue alanine (A) at amino acid position 234 of SEQ ID NO: 1 (A234T); a substitution of glutamine (Q) for the wild type residue arginine (R) at amino acid position 243 of SEQ ID NO: 1 (R243Q); a substitution of histidine (H) for the wild type residue arginine (R) at amino acid position 316 of SEQ ID NO: 1 (R316H); and a substitution of threonine (T) for the wild type residue alanine (A) at amino acid position 317 of SEQ ID NO: 1 (A317T).

In some embodiments, the subject is sensitive to resmetirom, as demonstrated by a significant increase in the concentration of sex hormone-binding globulin (SHBG) in the subject after the subject's exposure to resmetirom.

In some embodiments, the subject has ABCG2 rs2231142, which is a BCRP polymorphism.

In some embodiments, the subject has a Cyp2C8 polymorphism that inhibits the metabolite formation of resmetirom.

In some embodiments, the subject has hepatic impairment. In some embodiments, the hepatic impairment is NASH. Accordingly, the combination therapy described herein avoids atorvastatin which has complications in NASH patients with hepatic impairment. In some embodiments, the subject is not currently administered atorvastatin or the subject is intolerant to atorvastatin. It was discovered that there is unfavorable interaction between atorvastatin and resmetirom.

In some embodiments, the subject is a mammal.

In some embodiments, the subject is a human.

In some embodiments, the present disclosure provides a method of treating a liver disorder or a lipid disorder in a subject in need thereof, the method comprising administering to the subject rosuvastatin in a range of about 1 mg to 40 mg, and resmetirom in a range of about 40 mg to 200 mg.

In some embodiments, the present disclosure provides the use of rosuvastatin and resmetirom in the manufacture of a medicament for treating a liver disorder or a lipid disorder in a subject in need thereof, wherein rosuvastatin is in a range of about 1 mg to 40 mg, and resmetirom is in a range of about 40 mg to 200 mg.

In some embodiments, the present disclosure provides rosuvastatin and resmetirom for use in a method of treating a liver disorder or a lipid disorder in a subject in need thereof, wherein the method comprises administering to the subject rosuvastatin in a range of about 1 mg to 40 mg, and resmetirom in a range of about 40 mg to 200 mg.

In some embodiments, the present disclosure provides a method of treating a liver disorder or a lipid disorder in a subject in need thereof, the method comprising administering to the subject rosuvastatin in a combination therapy with resmetirom, wherein rosuvastatin is in a range of about 1 mg to 40 mg, and resmetirom is in a range of about 40 mg to 200 mg.

In some embodiments, the present disclosure provides the use of rosuvastatin in a combination therapy with resmetirom in the manufacture of a medicament for treating a liver disorder or a lipid disorder in a subject in need thereof, wherein rosuvastatin is in a range of about 1 mg to 40 mg, and resmetirom is in a range of about 40 mg to 200 mg.

In some embodiments, the present disclosure provides rosuvastatin for use in a combination therapy with resmetirom in treating a liver disorder or a lipid disorder in a subject in need thereof, wherein the combination therapy comprises administering to the subject rosuvastatin in a range of about 1 mg to 40 mg, and resmetirom in a range of about 40 mg to 200 mg.

In some embodiments, the present disclosure provides a pharmaceutical composition comprising rosuvastatin in a range of about 1 mg to 40 mg, resmetirom in a range of about 40 mg to 200 mg, and a pharmaceutically acceptable excipient. The pharmaceutical composition can be used in a method of treating a liver disorder or a lipid disorder in a subject in need thereof.

In some embodiments, the present disclosure provides a pharmaceutical composition comprising rosuvastatin in a range of about 1 mg to 40 mg and a pharmaceutically acceptable excipient, for use in a combination therapy with resmetirom in treating a liver disorder or a lipid disorder in a subject in need thereof, wherein resmetirom is administered in a range of about 40 mg to 200 mg.

The dose for therapeutic or prophylactic purposes of rosuvastatin and resmetirom will naturally vary according to the nature and severity of the conditions, the age and sex of the subject and the route of administration, according to well-known principles of medicine.

In some embodiments, the dose of rosuvastatin administered is in a range of about 1 mg to 40 mg. In some embodiments, the dose of rosuvastatin administered is in a range of about 1 mg to 30 mg. In some embodiments, the dose of rosuvastatin administered is in a range of about 1 mg to 20 mg. In some embodiments, the dose of rosuvastatin administered is in a range of about 1 mg to 10 mg. In some embodiments, the dose of rosuvastatin administered is in a range of about 1 mg to 5 mg.

In some embodiments, the dose of rosuvastatin administered is in a range of about 5 mg to 40 mg. In some embodiments, the dose of rosuvastatin administered is in a range of about 5 mg to 30 mg. In some embodiments, the dose of rosuvastatin administered is in a range of about 5 mg to 20 mg. In some embodiments, the dose of rosuvastatin administered is in a range of about 5 mg to 10 mg. In some embodiments, the dose of rosuvastatin administered is in a range of about 10 mg to 40 mg. In some embodiments, the dose of rosuvastatin administered is in a range of about 10 mg to 30 mg. In some embodiments, the dose of rosuvastatin administered is in a range of about 10 mg to 20 mg. In some embodiments, the dose of rosuvastatin administered is in a range of about 20 mg to 40 mg. In some embodiments, the dose of rosuvastatin administered is in a range of about 20 mg to 30 mg. In some embodiments, the dose of rosuvastatin administered is in a range of about 30 mg to 40 mg.

In some embodiments, the dose of rosuvastatin administered is about 1 mg. In some embodiments, the dose of rosuvastatin administered is about 2 mg. In some embodiments, the dose of rosuvastatin administered is about 3 mg. In some embodiments, the dose of rosuvastatin administered is about 4 mg. In some embodiments, the dose of rosuvastatin administered is about 5 mg. In some embodiments, the dose of rosuvastatin administered is about 6 mg. In some embodiments, the dose of rosuvastatin administered is about 7 mg. In some embodiments, the dose of rosuvastatin administered is about 8 mg. In some embodiments, the dose of rosuvastatin administered is about 9 mg. In some embodiments, the dose of rosuvastatin administered is about 10 mg. In some embodiments, the dose of rosuvastatin administered is about 11 mg. In some embodiments, the dose of rosuvastatin administered is about 12 mg. In some embodiments, the dose of rosuvastatin administered is about 13 mg. In some embodiments, the dose of rosuvastatin administered is about 14 mg. In some embodiments, the dose of rosuvastatin administered is about 15 mg. In some embodiments, the dose of rosuvastatin administered is about 20 mg. In some embodiments, the dose of rosuvastatin administered is about 25 mg. In some embodiments, the dose of rosuvastatin administered is about 30 mg. In some embodiments, the dose of rosuvastatin administered is about 35 mg. In some embodiments, the dose of rosuvastatin administered is 40 mg.

In some embodiments, the dose of resmetirom administered is in a range of about 40 to 200 mg. In some embodiments, the dose of resmetirom administered is in a range of about 40 to 180 mg. In some embodiments, the dose of resmetirom administered is in a range of about 40 to 160 mg. In some embodiments, the dose of resmetirom administered is in a range of about 40 to 140 mg. In some embodiments, the dose of resmetirom administered is in a range of about 40 to 120 mg. In some embodiments, the dose of resmetirom administered is in a range of about 40 to 100 mg. In some embodiments, the dose of resmetirom administered is in a range of about 40 to 80 mg. In some embodiments, the dose of resmetirom administered is in a range of about 40 to 60 mg. In some embodiments, the dose of resmetirom administered is in a range of about 40 to 50 mg.

In some embodiments, the dose of resmetirom administered is in a range of about 50 to 200 mg. In some embodiments, the dose of resmetirom administered is in a range of about 50 to 180 mg. In some embodiments, the dose of resmetirom administered is in a range of about 50 to 160 mg. In some embodiments, the dose of resmetirom administered is in a range of about 50 to 140 mg. In some embodiments, the dose of resmetirom administered is in a range of about 50 to 120 mg. In some embodiments, the dose of resmetirom administered is in a range of about 50 to 100 mg. In some embodiments, the dose of resmetirom administered is in a range of about 50 to 80 mg. In some embodiments, the dose of resmetirom administered is in a range of about 50 to 60 mg.

In some embodiments, the dose of resmetirom administered is in a range of about 60 to 200 mg. In some embodiments, the dose of resmetirom administered is in a range of about 60 to 180 mg. In some embodiments, the dose of resmetirom administered is in a range of about 60 to 160 mg. In some embodiments, the dose of resmetirom administered is in a range of about 60 to 140 mg. In some embodiments, the dose of resmetirom administered is in a range of about 60 to 120 mg. In some embodiments, the dose of resmetirom administered is in a range of about 60 to 100 mg. In some embodiments, the dose of resmetirom administered is in a range of about 60 to 80 mg.

In some embodiments, the dose of resmetirom administered is in a range of about 70 to 200 mg. In some embodiments, the dose of resmetirom administered is in a range of about 70 to 180 mg. In some embodiments, the dose of resmetirom administered is in a range of about 70 to 160 mg. In some embodiments, the dose of resmetirom administered is in a range of about 70 to 140 mg. In some embodiments, the dose of resmetirom administered is in a range of about 70 to 120 mg. In some embodiments, the dose of resmetirom administered is in a range of about 70 to 100 mg. In some embodiments, the dose of resmetirom administered is in a range of about 70 to 80 mg.

In some embodiments, the dose of resmetirom administered is in a range of about 80 to 200 mg. In some embodiments, the dose of resmetirom administered is in a range of about 80 to 180 mg. In some embodiments, the dose of resmetirom administered is in a range of about 80 to 160 mg. In some embodiments, the dose of resmetirom administered is in a range of about 80 to 140 mg. In some embodiments, the dose of resmetirom administered is in a range of about 80 to 120 mg. In some embodiments, the dose of resmetirom administered is in a range of about 80 to 100 mg.

In some embodiments, the dose of resmetirom administered is in a range of about 100 to 200 mg. In some embodiments, the dose of resmetirom administered is in a range of about 100 to 180 mg. In some embodiments, the dose of resmetirom administered is in a range of about 100 to 160 mg. In some embodiments, the dose of resmetirom administered is in a range of about 100 to 140 mg. In some embodiments, the dose of resmetirom administered is in a range of about 100 to 120 mg.

In some embodiments, the dose of resmetirom administered is about 40 mg. In some embodiments, the dose of resmetirom administered is about 50 mg. In some embodiments, the dose of resmetirom administered is about 60 mg. In some embodiments, the dose of resmetirom administered is about 70 mg. In some embodiments, the dose of resmetirom administered is about 80 mg. In some embodiments, the dose of resmetirom administered is about 90 mg. In some embodiments, the dose of resmetirom administered is about 100 mg. In some embodiments, the dose of resmetirom administered is about 110 mg. In some embodiments, the dose of resmetirom administered is about 120 mg. In some embodiments, the dose of resmetirom administered is about 130 mg. In some embodiments, the dose of resmetirom administered is about 140 mg. In some embodiments, the dose of resmetirom administered is about 150 mg. In some embodiments, the dose of resmetirom administered is about 160 mg. In some embodiments, the dose of resmetirom administered is about 170 mg. In some embodiments, the dose of resmetirom administered is about 180 mg. In some embodiments, the dose of resmetirom administered is about 190 mg. In some embodiments, the dose of resmetirom administered is about 200 mg.

In some embodiments, rosuvastatin and resmetirom are administered once daily. In some embodiments, rosuvastatin and resmetirom are administered twice daily. In some embodiments, rosuvastatin and resmetirom are administered three times daily.

In some embodiments, the rosuvastatin and resmetirom are administered in temporal proximity. In some embodiments, rosuvastatin is administered before resmetirom. In some embodiments, resmetirom is administered before rosuvastatin.

In some embodiments, the rosuvastatin and resmetirom are administered simultaneously. In some embodiments, the rosuvastatin and resmetirom are administered simultaneously as separate compositions.

In some embodiments, the rosuvastatin and resmetirom are administered in a single composition.

In some embodiments, the rosuvastatin and resmetirom are administered separately.

In some embodiments, effective exposure of rosuvastatin and resmetirom is achieved when administered simultaneously. Without wishing to be bound by theory, as resmetirom and rosuvastatin are both substrates for BCRP and OSTαβ-both are drug transporters concentrated in the gut, simultaneous administration of both drugs may potentiate the exposure of each other in the gut as they compete with each other for BCRP and OSTαβ. As a result, rosuvastatin can be administered at a lower dose than what is currently prescribed, thereby reducing or eliminating the side effects (e.g., myopathy) of high dose rosuvastatin.

In some embodiments, the rosuvastatin and resmetirom are administered in the morning hours of the day. In some embodiments, the rosuvastatin and resmetirom are administered in the evening hours of the day. In some embodiments, the rosuvastatin and resmetirom are administered before sleep.

The compounds of the disclosure or pharmaceutical compositions comprising these compounds may be administered to a subject by any convenient route of administration, whether systemically/peripherally or locally (i.e., at the site of desired action). In some embodiments, the compounds of the disclosure or pharmaceutical compositions comprising these compounds may be injected to the liver.

Routes of administration include, but are not limited to, oral (e.g. by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

In some embodiments, rosuvastatin and/or resmetirom are administered orally.

In some embodiments, rosuvastatin and/or resmetirom are administered intravenously.

In some embodiments, rosuvastatin and/or resmetirom are administered by direct injection.

The combination therapy described herein can also be used to prevent a liver disease or disorder and/or a lipid disease or disorder.

Pharmaceutical Compositions

In some aspects, the present disclosure provides a pharmaceutical composition comprising a compound or compounds of the present disclosure as an active ingredient. In some embodiments, the present disclosure provides a pharmaceutical composition comprising rosuvastatin and resmetirom, or pharmaceutically acceptable salts or solvates thereof, and one or more pharmaceutically acceptable carriers or excipients.

The pharmaceutical compositions of the present disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

The compounds of present disclosure can be formulated for oral administration in forms such as tablets, capsules (each of which includes sustained release or timed release formulations), powder-in-capsules, pills, powders, granules, elixirs, tinctures, suspensions, syrups and emulsions. The compounds of present disclosure on can also be formulated for intravenous (bolus or in-fusion), intraperitoneal, topical, subcutaneous, intramuscular or transdermal (e.g., patch) administration, all using forms well known to those of ordinary skill in the pharmaceutical arts.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

The formulation of the present disclosure may be in the form of an aqueous solution comprising an aqueous vehicle. The aqueous vehicle component may comprise water and at least one pharmaceutically acceptable excipient. Suitable acceptable excipients include those selected from the group consisting of a solubility enhancing agent, chelating agent, preservative, tonicity agent, viscosity/suspending agent, buffer, and pH modifying agent, and a mixture thereof.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

In one embodiment, the active compounds are prepared with pharmaceutically acceptable excipients that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions (including liposomes targeted to infected cells with monoclonal antibodies to viral antigens) can also be used as pharmaceutically acceptable excipients.

The compositions of the disclosure may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

In some embodiments, the rosuvastatin is formulated in a gel.

In some embodiments, the rosuvastatin is formulated in a tablet.

In some embodiments, the rosuvastatin is formulated in a pill.

In some embodiments, the rosuvastatin is formulated in a capsule.

In some embodiments, the rosuvastatin is formulated in a solution.

In some embodiments, the resmetirom is formulated in a gel.

In some embodiments, the resmetirom is formulated in a tablet.

In some embodiments, the resmetirom is formulated in a pill.

In some embodiments, the resmetirom is formulated in a capsule.

In some embodiments, the resmetirom is formulated in a solution.

In some embodiments, the pharmaceutical composition is formulated in a gel.

In some embodiments, the pharmaceutical composition is formulated in a tablet.

In some embodiments, the pharmaceutical composition is formulated in a pill.

In some embodiments, the pharmaceutical composition is formulated in a capsule.

In some embodiments, the pharmaceutical composition is formulated in a solution.

Definitions

Unless otherwise defined, all technical and scientific terms used herein have the same meaning as commonly understood by one of ordinary skill in the art to which this disclosure belongs. The terminology used in the description is intended to describe particular embodiments only, and is not intended to limit the scope of the invention.

Where a range of values is provided, it is understood that the range includes both of the endpoints with that range, as well as all intervening values.

The following terms are used to describe the present disclosure. In instances where a term is not specifically defined herein, that term is given an art-recognized meaning by those of ordinary skill applying that term in context to its use in describing the present invention.

As used herein, "rosuvastatin" refers to (E)-7-[4-(4-fluorophenyl)-6-isopropyl-2-[methyl(methylsulfonyl)amino] pyrimidin-5-yl](3R,5S)-3,5-dihydroxyhept-6-enoic acid (i.e.. 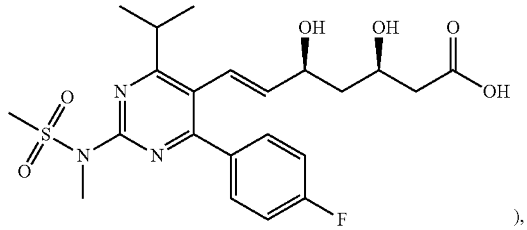 ), or bis[(E)-7-[4-(4-fluorophenyl)-6-isopropyl-2-[methyl (methylsulfonyl)amino] pyrimidin-5-yl](3R,5S)-3,5-dihydroxyhept-6-enoic acid] calcium salt (i.e., 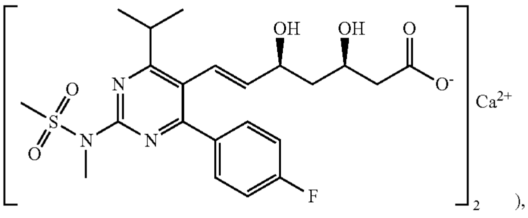 ), or any other of its pharmaceutically acceptable salts.

As used herein, "resmetirom" refers to MGL-3196 or 2-(3,5-dichloro-4-((5-isopropyl-6-oxo-1,6-dihydropyridazin-3-yl)oxy)phenyl)-3,5-dioxo-2,3,4,5-tetrahydro-1,2,4-triazine-6-carbonitrile (i.e., 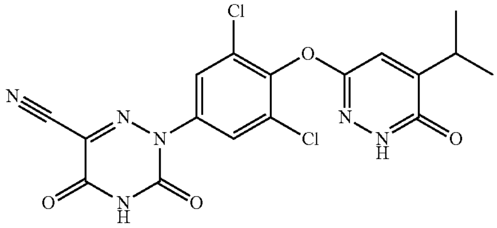 ), or any of its pharmaceutically acceptable salts.

The articles "a" and "an" as used herein and in the appended claims are used herein to refer to one or to more than one (i.e., to at least one) of the grammatical object of the article unless the context clearly indicates otherwise. By way of example, "an ultrapure form" means one ultrapure form or more than one ultrapure form.

The phrase "and/or," as used herein in the specification and in the claims, should be understood to mean "either or both". Other elements may optionally be present other than the elements specifically identified by the "and/or" clause. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements).

Unless explicitly indicated otherwise, the terms "approximately" and "about" are synonymous. In some embodiments, "approximately" and "about" refer to the recited amount, value, dose or duration ±10%, ±8%, ±6%, ±5%, ±4%, ±2%, ±1%, or ±0.5%. In some embodiments, "approximately" and "about" refer to the listed amount, value, dose, or duration ±5%. In some embodiments, "approximately" and "about" refer to the listed amount, value, dose, or duration ±2%. In some embodiments, "approximately" and "about" refer to the listed amount, value, dose, or duration ±1%.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

The term "combination therapy" can refer to both concurrent administration (administration of two or more therapeutic agents at the same time) and administration with temporal proximity, as long as the therapeutic agents are present in the patient to some extent, preferably at effective amounts, at the same time.

The term "effective" can mean, but is in no way limited to, that amount/dose of the active pharmaceutical ingredient, which, when used in the context of its intended use, effectuates or is sufficient to prevent, inhibit the occurrence, ameliorate, delay or treat (alleviate a symptom to some extent, preferably all) the symptoms of a liver disorder or a lipid disorder in a subject in need of such treatment or receiving such treatment. The term "effective" subsumes all other effective amount or effective concentration terms, e.g., "effective amount/dose," "pharmaceutically effective amount/dose" or "therapeutically effective amount/dose," which are otherwise described or used in the present application.

The effective amount depends on the age, weight, gender, previous patient history or family history, type and severity of disease, the composition used, the route of administration, the stage of treatment, the type of mammal being treated, the physical characteristics of the specific mammal under consideration, concurrent medication, and other factors which those skilled in the medical arts will recognize. The exact amount can be ascertainable by one skilled in the art using known techniques in view of clinical data and medical experience (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

As used herein, the term "preventing" or "prevent" describes reducing or eliminating the onset of the symptoms or complications of a disease, condition, or disorder.

As used herein, the term "salt" is a pharmaceutically acceptable salt and can include acid addition salts including hydrochlorides, hydrobromides, phosphates, sulphates, hydrogen sulphates, alkylsulphonates, arylsulphonates, acetates, benzoates, citrates, maleates, fumarates, succinates, lactates, and tartrates. A salt can also be formed between a cation and a negatively charged group on Compound A. Suitable cations include sodium ion, potassium ion, magnesium ion, calcium ion, and an ammonium cation such as tetramethylammonium ion. Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. A salt can also contain a quaternary nitrogen atom.

As used herein, the term "subject" is interchangeable with the term "subject in need thereof", both of which refer to a subject having a disease or disorder or having an increased risk of developing the disease or disorder. A "subject" includes a mammal. The mammal can be, e.g., a human or appropriate non-human mammal, such as primate, mouse, rat, dog, cat, cow, horse, goat, camel, sheep or a pig. In one embodiment, the mammal is a human. A subject in need thereof can be one who has been previously diagnosed or identified as having a disease or disorder disclosed herein. A subject in need thereof can also be one who is suffering from a disease or disorder disclosed herein. Alternatively, a subject in need thereof can be one who has an increased risk of developing such disease or disorder relative to the population at large (i.e., a subject who is predisposed to developing such disorder relative to the population at large). A subject in need thereof can have a refractory or resistant a disease or disorder disclosed herein (i.e., a disease or disorder disclosed herein that does not respond or has not yet responded to treatment). The subject may be resistant at start of treatment or may become resistant during treatment. In some embodiments, the subject in need thereof received and failed all known effective therapies for a disease or disorder disclosed herein. In some embodiments, the subject in need thereof received at least one prior therapy.

As used herein, "temporal proximity" means that administration of one therapeutic agent occurs within a time period before or after the administration of another therapeutic agent, such that the therapeutic effect of the one therapeutic agent overlaps with the therapeutic effect of the another therapeutic agent. In some embodiments, the therapeutic effect of the one therapeutic agent completely overlaps with the therapeutic effect of the another therapeutic agent. In some embodiments, "temporal proximity" means that administration of one therapeutic agent occurs within a time period before or after the administration of another therapeutic agent, such that there is a synergistic effect between the one therapeutic agent and the another therapeutic agent. "Temporal proximity" may vary according to various factors, including but not limited to, the age, gender, weight, genetic background, medical condition, disorder, disease history, and treatment history of the subject to which the therapeutic agents are to be administered; the disease, disorder, or condition to be treated or ameliorated; the therapeutic outcome to be achieved; the dosage, dosing frequency, and dosing duration of the therapeutic agents; the pharmacokinetics and pharmacodynamics of the therapeutic agents; and the route(s) through which the therapeutic agents are administered. In some embodiments, "temporal proximity" means within 15 minutes, within 30 minutes, or within an hour. In some embodiments, multiple administration of one therapeutic agent can occur in temporal proximity to a single administration of another therapeutic agent. In some embodiments, temporal proximity may change during a treatment cycle or within a dosing regimen. In some embodiments, two therapeutic agents are administered in temporal proximity such that maximal gastrointestinal and systemic exposure to both therapeutic agents occurs at about the same time.

It is to be appreciated that references to "treating" or "treatment" include the alleviation of established symptoms of a condition or disorder. "Treating" or "treatment" of a state, disorder, or condition therefore includes: (1) delaying the appearance of clinical symptoms of the state, disorder, or condition developing in a human that may be afflicted with the state, disorder, or condition but does not yet experience or display clinical or subclinical symptoms of the state, disorder, or condition, (2) inhibiting the state, disorder, or condition, i.e., arresting or reducing the development of the disease or a relapse thereof (in case of maintenance treatment) or at least one clinical or subclinical symptom thereof, or (3) relieving or attenuating the disease, i.e., causing regression of the state, disorder, or condition or at least one of its clinical or subclinical symptoms.

EXAMPLES

Example 1. Resmetirom Effects on Plasma Levels of Rosuvastatin

In a clinical drug-drug interaction (DDI) study conducted between resmetirom and rosuvastatin, no safety issues were observed such as liver enzyme or creatine kinase (CK) elevations that might be related to concomitant statin dosing. Minimal effect (<2-fold) of 200 mg of resmetirom to increase rosuvastatin levels were found. Based on these results and in vitro/in vivo predictions, the potential impact of resmetirom on statin pharmacokinetics (PK) according to the dose of resmetirom is shown in Table 1.

TABLE 1

Summary Predictions for AUC Increases for Rosuvastatin, by Resmetirom Dose and Assumed High Liver:Blood Ratio

| | Predicted by Dose of Resmetirom | | | | Observed 200 mg |
|---|---|---|---|---|---|
| | 50 mg | 80 mg | 100 mg | 200 mg | (03 study) |
| Rosuvastatin | 1.42 | 1.55 | 1.60 | 1.79 | 1.82 |

In this study, low dose of rosuvastatin (10 mg, with the top marketed dose being 40 mg) is selected to minimize the possibility of dose-related side effects, but also above the lowest dose so as to allow a better description of the terminal elimination phase of its plasma concentration; and resmetirom dose (200 mg) is selected because a higher dose would more fully test the potential for drug-drug interaction.

TABLE 2

Summary of the PK Parameters of Rosuvastatin in Healthy Subjects after a Single Dose of 10 mg Rosuvastatin in the Presence and the Absence of 200 mg/day MGL 3196

| | Rosuvastatin | | | | | | | |
|---|---|---|---|---|---|---|---|---|
| | Absence MGL-3196 | | | | Presence of MGL-3196 | | | |
| PK Parameter | N | Mean | SD | % CV | N | Mean | SD | % CV |
| $C_{max}$, ng/mL | 25 | 3.62 | 2.04 | 56.5 | 25 | 10.6 | 6.19 | 58.2 |
| $T_{max}$, h | 25 | 4.56 | 0.821 | 18.0 | 25 | 4.60 | 1.22 | 26.6 |
| $AUC_{last}$, ng · h/mL | 25 | 44.5 | 22.9 | 51.3 | 25 | 85.2 | 48.0 | 56.3 |
| $AUC_{inf}$, ng · h/mL | 22 | 51.7 | 22.8 | 44.1 | 24 | 92.4 | 47.2 | 51.1 |
| % $AUC_{exts}$ | 25 | 10.6 | 6.13 | 57.7 | 25 | 6.59 | 4.76 | 72.2 |
| λ, $h^{-1}$ | 25 | 0.0414 | 0.0145 | 35.1 | 25 | 0.0398 | 0.0108 | 27.2 |
| $T_{1/2}$, h | 25 | 18.2 | 4.93 | 27.1 | 25 | 18.6 | 4.68 | 25.2 |

TABLE 3

| Summary of the Results of Rosuvastatin in Healthy Subjects in the Presence or the Absence of MGL 3196 | | | | | |
|---|---|---|---|---|---|
| | Rosuvastatin Geometric Mean | | | | |
| PK Parameter | Absence MGL-3196 | Presence of MGL-3196 | % Ratio[a] | CI 90% Lower[b] | CI 90% Upper[c] |
| $C_{max}$, ng/mL | 3.11 | 9.09 | 292.20 | 247.43 | 345.07 |
| $AUC_{last}$, ng · h/mL | 38.0 | 73.3 | 192.76 | 167.63 | 221.67 |
| $AUC_{inf}$, ng · h/mL | 46.6 | 85.1 | 182.41 | 161.41 | 206.15 |

[a]% Ratio of rosuvastatin geometric means with MGL-3196 to without MGL-3196

[b]CI90% Lower—Lower Levels of the 90% Confidence Intervals

[c]CI90% Upper—Upper Levels of the 90% Confidence Intervals

The results indicate that MGL-3196 200 mg/day for 9 consecutive days increased the $AUC_{inf}$ of single-dose rosuvastatin ∇182.4% (90% CI: 161.4 to 206.15%), and appeared to slightly decrease the geometric mean ratio of $AUC_{inf}$ of N-desmethyl rosuvastatin relative to that of rosuvastatin.

Example 2. MGL-3196 in HeFH Patients

A Phase 2 clinical trial was conducted in 116 patients with proven heterozygous familial hypercholesterolemia (HeFH). The primary endpoint was reduction in LDL-C compared with placebo and secondary endpoints included effects on additional lipids and lipoproteins.

MGL-3196-06 (NCT03038022) was a 12-week multi-center, randomized, double blind, placebo-controlled trial in HeFH patients not at LDL-C target on maximally tolerated statins. Patients received MGL-3196 100 mg or placebo once daily for 12 weeks (in a 2:1 ratio) in addition to their LDL-C lowering regimen.

Approximately 75% of patients were on high intensity statins (atorvastatin (also referred to as "atorva") 80 mg; rosuvastatin (also referred to as "rosuva") 20/40 mg); 25.9% were on no or moderate statin doses (up to 40 mg atorva).

Figure 2:
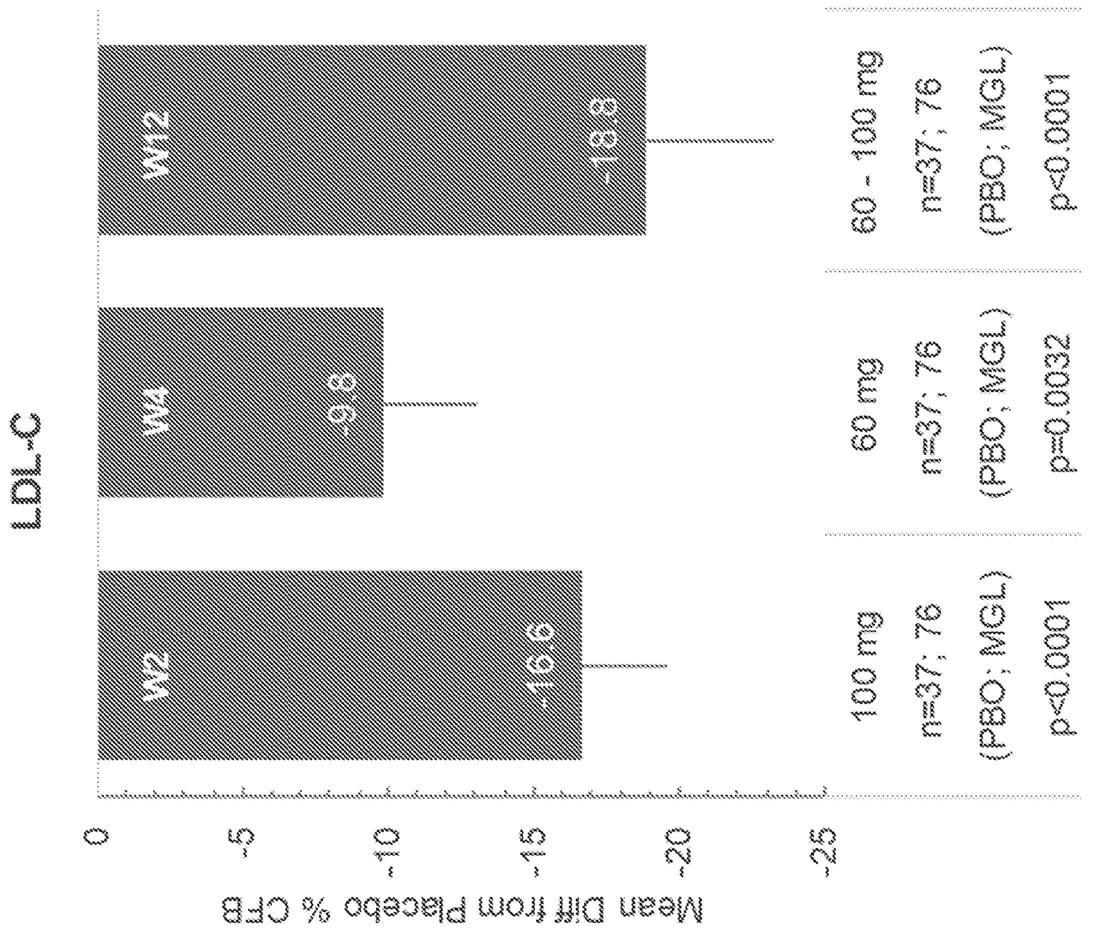
FIG. 2 is a graph showing the change from baseline (CFB) of LDL-C in patients on an LDL-C lowering regimen receiving MGL-3196 compared to the placebo at weeks 2, 4, and 12 (denoted as W2, W4, and W12 respectively).
Figure 3:
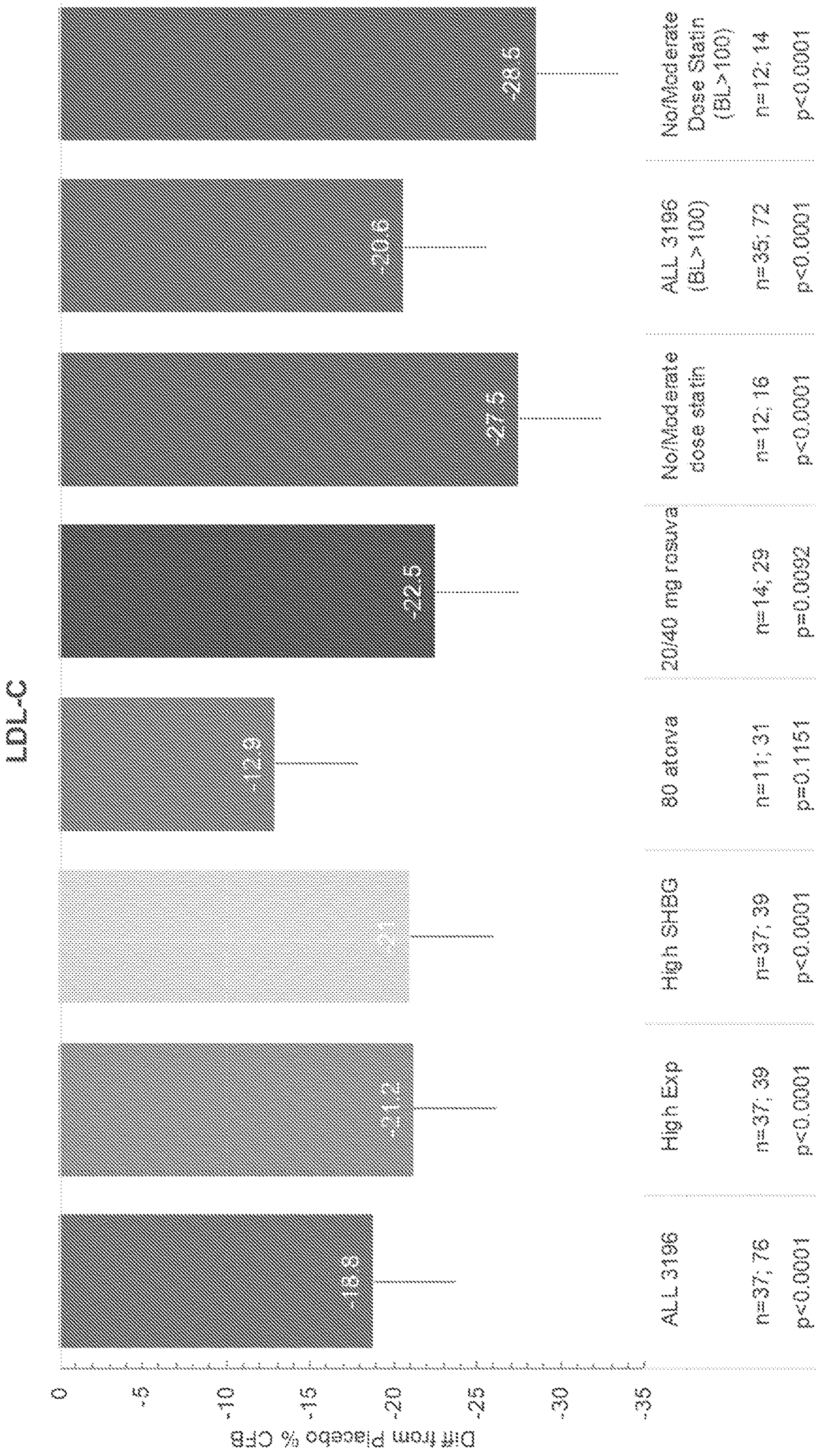
FIG. 3 is a graph showing the CFB of LDL-C in patients on a specific LDL-C lowering regimen receiving MGL-3196 compared to the placebo at 12 weeks. MGL-3196-treated individuals are grouped into a high exposure group ("high exp") with an AUC in week 2 of >5000 mg*h/mL, and "high SHBG" refers to a group of individuals with a high SHBG increase ≥140% change from baseline. "No/Moderate Dose Statin" refers to individuals not able to tolerate statins combined with individuals taking statins but demonstrating resistance to achieving the desired lipid lowering effect. "BL>100" refers to individuals with >100 mg/dL of LDL-C at baseline.

MGL-3196 treated patients achieved (p<0.0001) LDL-C lowering compared with placebo (see, for example, FIGS. 2 and 3). LDL-C lowering reached 28.5% compared to placebo in a prespecified group of MGL-3196-treated patients intolerant of high intensity statin doses.

Figure 4:
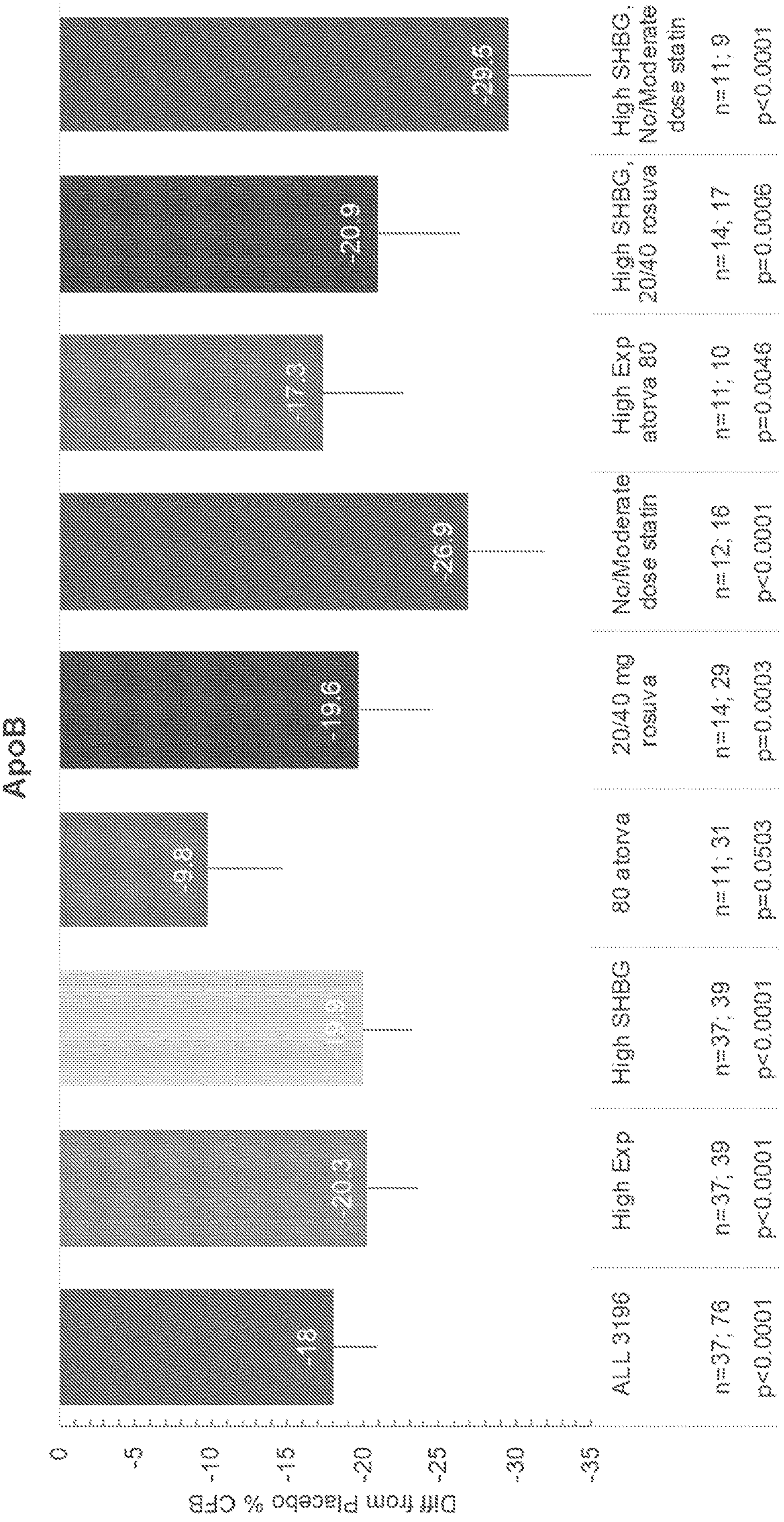
FIG. 4 is a graph showing the CFB of apolipoprotein B (ApoB) in patients on a specific LDL-C lowering regimen receiving MGL-3196 compared to the placebo at 12 weeks. MGL-3196-treated individuals are grouped into a high exposure group ("high exp") with an AUC in week 2 of >5000 mg*h/mL, and "high SHBG" refers to a group of individuals with a high SHBG increase ≥140% change from baseline. "No/Moderate Dose Statin" refers to individuals not able to tolerate statins combined with individuals taking statins but demonstrating resistance to achieving the desired lipid lowering effect.
Figure 5:
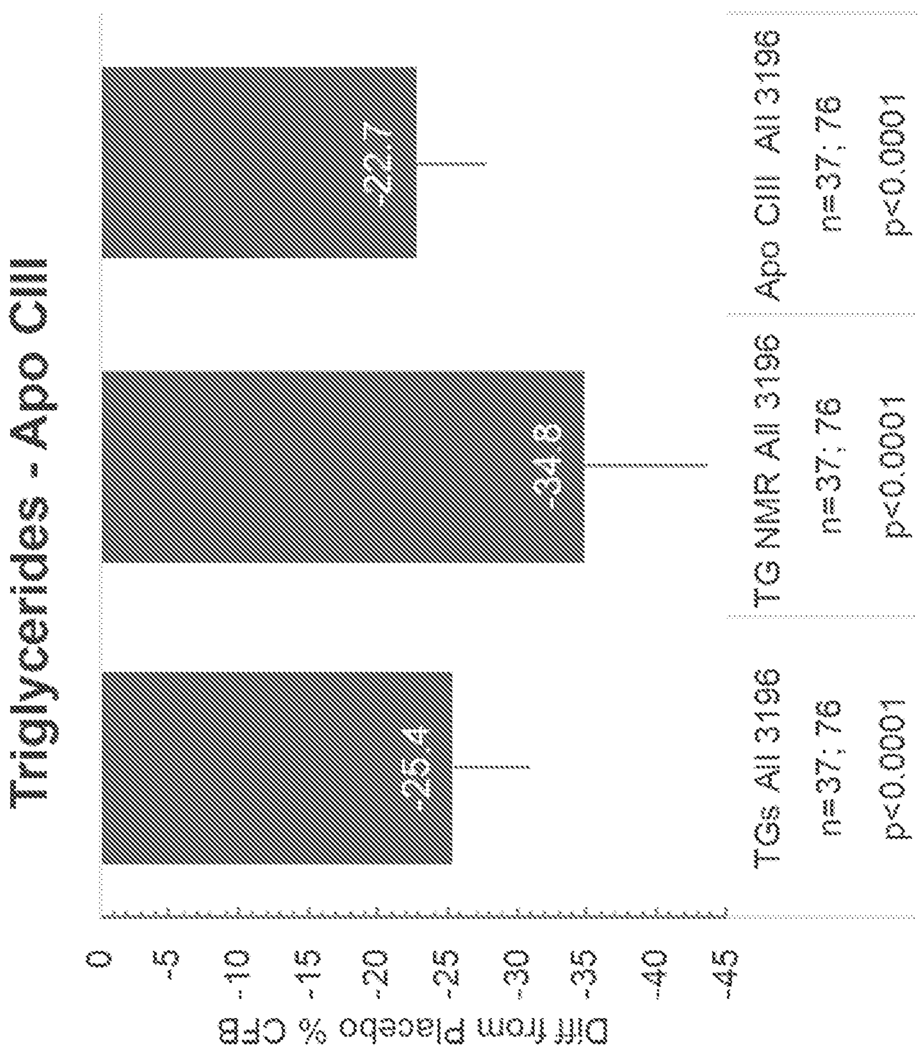
FIG. 5 is a graph showing the CFB of triglycerides (TGs) measured using a colorimetric clinical assay, triglycerides measured using nuclear magnetic resonance (NMR) and apolipoprotein CIII (Apo CIII) in patients on an LDL-C lowering regimen receiving MGL-3196 compared to the placebo at 12 weeks.
Figure 6:
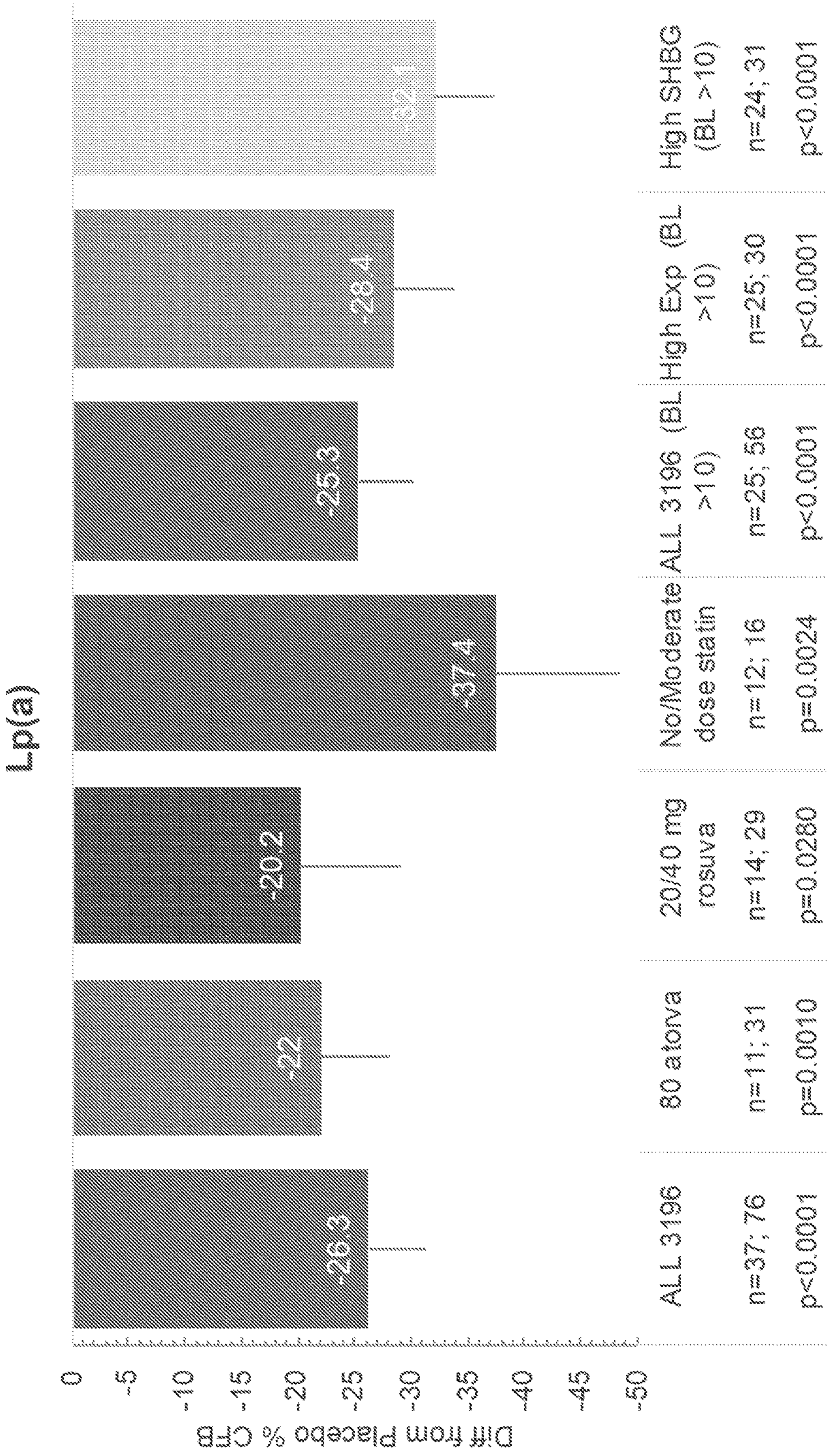
FIG. 6 is a graph showing the CFB of lipoprotein (a) (Lp(a)) in patients on a specific LDL-C lowering regimen receiving MGL-3196 compared to the placebo at 12 weeks. MGL-3196-treated individuals are grouped into a high exposure group ("high exp") with an AUC in week 2 of >5000 mg*h/mL, and "high SHBG" refers to a group of individuals with a high SHBG increase ≥140% change from baseline. "No/Moderate Dose Statin" refers to individuals not able to tolerate statins combined with individuals taking statins but demonstrating resistance to achieving the desired lipid lowering effect. "BL>10" refers to individuals with >10 mg/dL of Lp(a) at baseline.

Apolipoprotein B (ApoB) (−18-29%), Triglyceride (TG) (−25-31%), apolipoprotein CIII (Apo CIII) (−22%) and lipoprotein (a) (Lp(a)) (−26-33%) lowering were also observed (p<0.0001) (see, for example, FIGS. 4-6).

MGL-3196 statistically significantly lowers LDL-C and other atherogenic lipids in patients with HeFH and is effective in patients intolerant to high intensity statins. The effect of MGL-3196 to reduce multiple atherogenic lipids may lower coronary heart disease risk in NAFLD/NASH and mild to severely statin intolerant patients.

Example 3. MGL-3196 as a Substrate for BCRP

MGL-3196 is not an inhibitor of P-gp and is a moderate inhibitor of BCRP. Based on the predicted gut-wall BCRP interaction (R=33.5), there is a possible contribution of gut BCRP inhibition to drug interactions.

TABLE 4

| DDI R-value assessments | | | | |
|---|---|---|---|---|
| | $IC_{50}$ (μM) | Tissue | DDI assessment | R-value |
| BCRP | 27.4 | Intestine | $[I_2]/IC_{50} \geq 10$ | 33.5 |
| | | Biliary/renal/BBB | $[I_{free}]/IC_{50} \geq 0.02$ | 0.004 |

Example 4. MGL-3196 as a Substrate for OSTαβ

Figure 7:
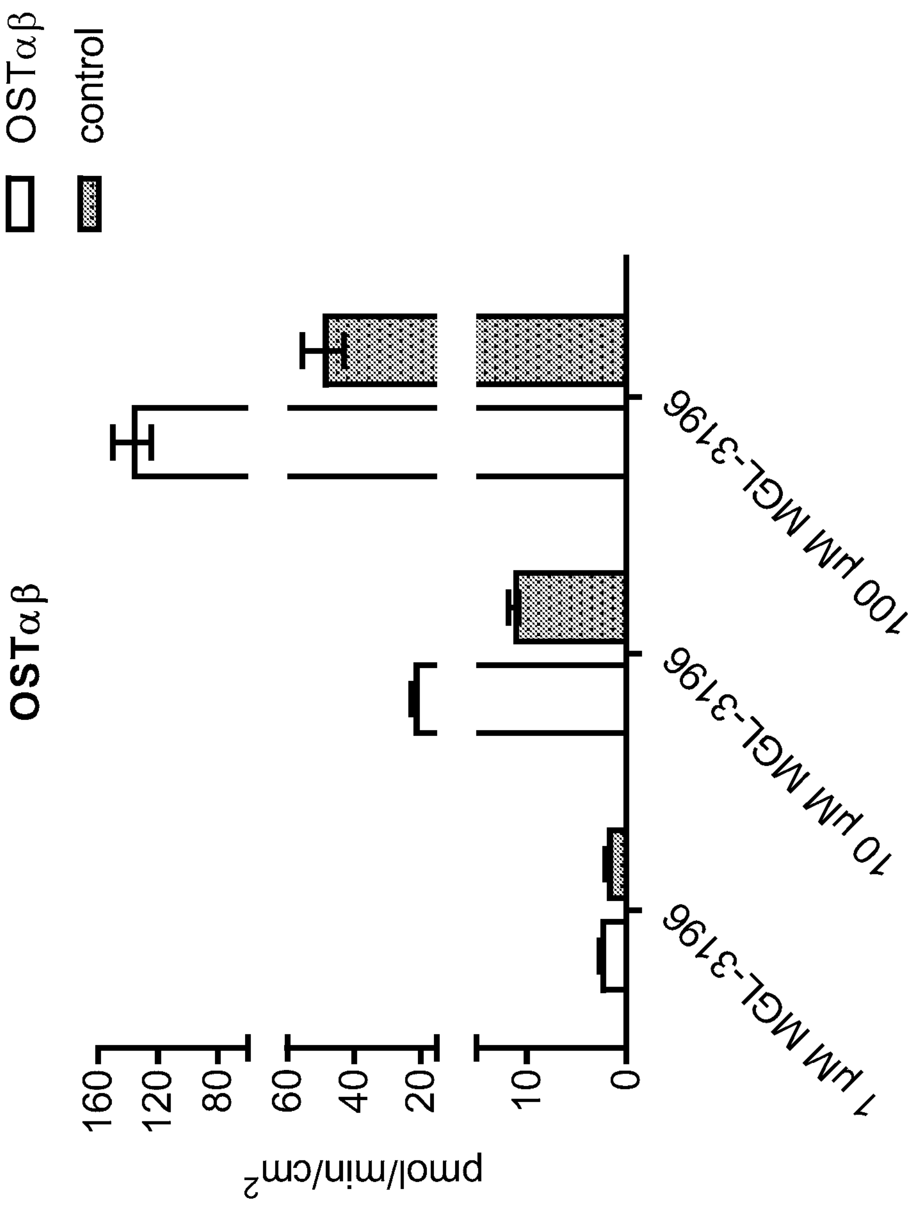
FIG. 7 shows the transport of MGL-3196 by human OSTαβ overexpressed in MDCK-II cells. Positive control transport was studied with 1 μM taurocholic acid.
Figure 8:
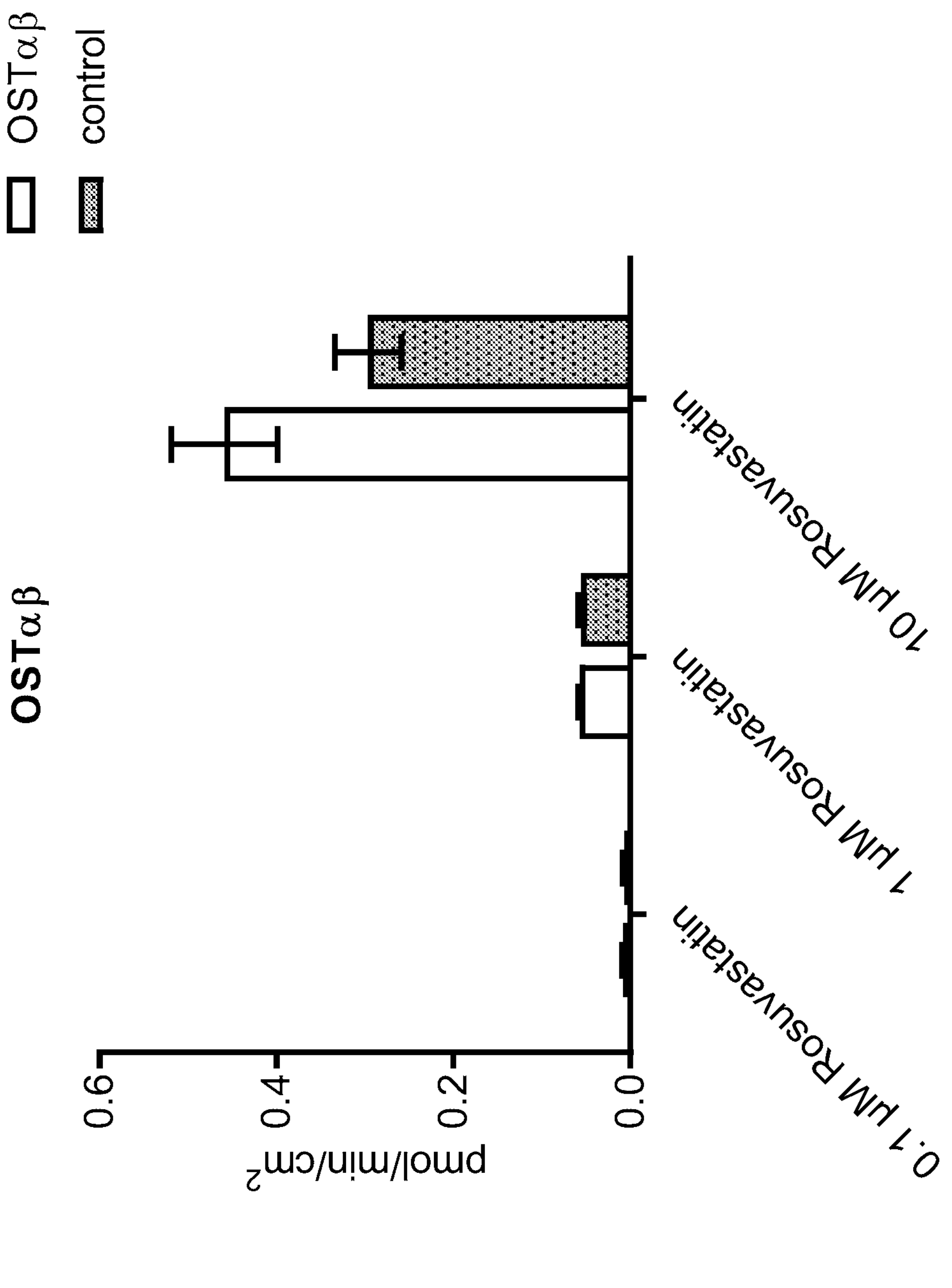
FIG. 8 shows the transport of rosuvastatin by human OSTαβ overexpressed in MDCK-II cells. Positive control transport was studied with 1 μM taurocholic acid.

MGL-3196 was tested as a potential substrate for human OSTαβ-mediated transport. At 10 μM and 100 μM of MGL-3196, there was more than a 2-fold difference of uptake observed in transporter-transfected cells compared to control cells for OSTαβ (see, for example, FIG. 7). At the lowest concentration of 1 μM MGL-3196, the uptake ratio was 1.35. In comparison, rosuvastatin tested at 0.1, 1 and 10 μM showed no greater than 2-fold uptake difference, with the largest uptake ratio of 1.55 being observed at 10 μM (see, for example, FIG. 8). Therefore, MGL-3196 may be a substrate for human OSTαβ under the study conditions. The probe substrate showed sufficient transport to satisfy the control criteria set by BioIVT.

TABLE 5

| In vitro data for the transport of MGL-3196 and rosuvastatin mediated by human OSTαβ | | | | |
|---|---|---|---|---|
| | | Accumulation of rosuvastatin or MGL-3196 (pmol/min/cm[2]) | | |
| Transporter | Assay Condition | In transporter cells | In control cells | Net |
| OSTαβ | 1 μM taurocholic acid | 0.109 ± 0.0105 | 0.0284 ± 0.000304 | 0.0809 ± 0.0105 |
| | 0.1 μM rosuvastatin | 0.00894 ± 0.000845 | 0.00664 ± 0.00215 | 0.00230 ± 0.000845 |
| | 1 μM rosuvastatin | 0.0575 ± 0.00167 | 0.0557 ± 0.00359 | 0.00176 ± 0.00167 |
| | 10 μM rosuvastatin | 0.459 ± 0.0599 | 0.297 ± 0.0377 | 0.162 ± 0.0599 |
| | 1 μM MGL-3196 | 2.58 ± 0.103 | 1.91 ± 0.220 | 0.670 ± 0.103 |
| | 10 μM MGL-3196 | 21.9 ± 0.810 | 11.3 ± 0.500 | 10.6 ± 0.810 |
| | 100 μM MGL-3196 | 137 ± 12.8 | 49.3 ± 6.28 | 88.1 ± 12.8 |

TABLE 6

| Uptake ratio from in vitro data for the transport of MGL-3196 and rosuvastatin mediated by human OSTαβ | | |
|---|---|---|
| Transporter | Assay Condition | Uptake ratio |
| OSTαβ | 1 μM taurocholic acid | 3.85 ± 0.370 |
| | 0.1 μM rosuvastatin | 1.35 ± 0.127 |
| | 1 μM rosuvastatin | 1.03 ± 0.0299 |
| | 10 μM rosuvastatin | 1.55 ± 0.202 |

TABLE 6-continued

| Uptake ratio from in vitro data for the transport of MGL-3196 and rosuvastatin mediated by human OSTαβ | | |
|---|---|---|
| Transporter | Assay Condition | Uptake ratio |
| | 1 μM MGL-3196 | 1.35 ± 0.0537 |
| | 10 μM MGL-3196 | 1.94 ± 0.0717 |
| | 100 μM MGL-3196 | 2.79 ± 0.260 |

EQUIVALENTS

While the present invention has been described in conjunction with the specific embodiments set forth above, many alternatives, modifications and other variations thereof will be apparent to those of ordinary skill in the art. All such alternatives, modifications, and variations are intended to fall within the spirit and scope of the present invention.

What is claimed is:

1. A method of treating a fatty liver disease in a human subject in need thereof, the method comprising administering to the human subject in need thereof an oral dose of 60 mg to 100 mg of resmetirom per day, wherein the human subject in need thereof is on a rosuvastatin regimen of 5 mg to 20 mg per day.

2. The method according to claim 1, wherein the fatty liver disease is non-alcoholic steatohepatitis (NASH).

3. The method according to claim 2, wherein the oral dose of resmetirom is 60 mg per day.

4. The method according to claim 2, wherein the oral dose of resmetirom is 80 mg per day.

5. The method according to claim 2, wherein the oral dose of resmetirom is 100 mg per day.

6. The method according to claim 2, comprising administering to the subject in need thereof a pharmaceutically acceptable oral dosage form comprising Form I resmetirom.

7. The method according to claim 2, wherein the rosuvastatin regimen is 10 mg per day.

8. The method according to claim 2, comprising administering to the human subject in need thereof a gel, a tablet, a pill, or a capsule comprising the oral dose of resmetirom.

9. The method according to claim 2, comprising administering to the human subject in need thereof a tablet comprising the oral dose of resmetirom.

10. The method according to claim 3, comprising administering to the human subject in need thereof a tablet comprising the oral dose of resmetirom.

11. The method according to claim 4, comprising administering to the human subject in need thereof a tablet comprising the oral dose of resmetirom.

12. The method according to claim 5, comprising administering to the human subject in need thereof a tablet comprising the oral dose of resmetirom.

13. The method according to claim 6, wherein the pharmaceutically acceptable oral dosage form is a tablet.

* * * * *